United States Patent [19]  [11] 4,256,754
Linhart et al.  [45] Mar. 17, 1981

[54] INSECTICIDAL AGENTS
[75] Inventors: Friedrich Linhart, Heidelberg; Bernd Zeeh, Ludwigshafen; Heinrich Adolphi, Limburgerhof, all of Fed. Rep. of Germany
[73] Assignee: BASF Aktiengesellschaft, Fed. Rep. of Germany
[21] Appl. No.: 59,186
[22] Filed: Jul. 20, 1979
[30] Foreign Application Priority Data
Jul. 28, 1978 [DE] Fed. Rep. of Germany ....... 2833193
[51] Int. Cl.³ .................... A01N 47/10; A01N 47/12
[52] U.S. Cl. .................................. 424/269; 424/200; 424/207; 424/210; 424/211; 424/212; 424/213; 424/216; 424/218; 424/220; 424/222; 424/225; 548/262
[58] Field of Search ............... 548/262; 424/269, 300, 424/251

[56] References Cited
U.S. PATENT DOCUMENTS
4,102,891  7/1978  Timmler et al. .................... 548/262

Primary Examiner—Richard Raymond
Attorney, Agent, or Firm—Keil & Witherspoon

[57] ABSTRACT

Insecticidal agents containing insecticidal active ingredients selected from the group consisting of carbamates, phosphoric (phosphonic) (di)(thio) acid esters, pyrethrins, pyrethroids, α-alkylphenyl acetates, α-cyclopropyl-phenyl acetates and chlorinated hydrocarbons, and, to increase the insecticidal action of these active ingredients, triazole derivatives or salts thereof.

The triazole derivatives have the formula

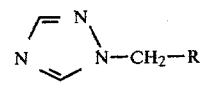

where R denotes unsubstituted or halogen-substituted phenyl, or

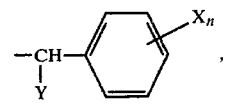

Y denoting hydrogen, halogen, alkylmercapto of 1 to 6 carbon atoms, alkenylmercapto of 2 to 6 carbon atoms, or unsubstituted or halogen-substituted phenylmercapto, X denoting halogen, and n denoting one of the integers zero, 1 and 2, with the proviso that n does not denote zero when Y is halogen.

8 Claims, No Drawings

INSECTICIDAL AGENTS

The present invention relates to insecticidal agents containing insecticidal active ingredients selected from the group consisting of carbamates, phosphoric (phosphonic) (di)(thio) acid esters, pyrethrins, pyrethroids, α-alkylphenyl acetates, α-cyclopropylphenyl acetates and chlorinated hydrocarbons, and, to increase the insecticidal action of these active ingredients, triazole derivatives.

It is known that, when chemical active ingredients are used to combat injurious organisms, mixtures thereof sometimes have a much greater effect than was to be expected from an addition of the individual actions. Such an increase in action is termed synergism. It is not necessary for the synergist itself to have a recognizable action on the organism to be combated.

For combating injurious insects, the synergists used almost exclusively in practice are piperonal derivatives. Piperonyl dioxide, which increases the action of pyrethrins, is of particular importance.

We have now found that insecticidal agents containing an insecticidally effective amount of a mixture of a triazole derivative of the formula

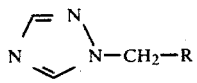

where R denotes unsubstituted or halogen-substituted phenyl, or

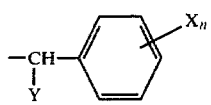

Y denoting hydrogen, halogen, alkylmercapto of 1 to 6 carbon atoms, alkenylmercapto of 2 to 6 carbon atoms, or unsubstituted or halogen-substituted phenylmercapto, X denoting halogen, and n denoting one of the integers zero, 1 and 2, with the proviso that n does not denote zero when Y is halogen, or a salt of a triazole derivative of the formula I, and an insecticidal active ingredient selected from the group consisting of carbamates, phosphoric (phosphonic) (di)(thio) acid esters, pyrethrins, pyrethroids, α-alkylphenyl acetates, α-cyclopropylphenyl acetates and chlorinated hydrocarbons, have a considerably greater insecticidal action than insecticidal agents containing the individual components.

The triazole derivatives of the formula I and the salts thereof are extremely effective synergists having a wide area of action. In addition to a particularly strong synergistic action on carbamates, they increase the action of insecticides from the group consisting of phosphoric or phosphonic acid esters and the corresponding thio or dithio esters, pyrethrins, pyrethroids, α-alkylphenyl acetates, α-cyclopropylphenyl acetates and chlorinated hydrocarbons.

Suitable synergistic triazole derivatives of the formula I are 1,2,4-triazoles, or salts thereof, which bear, in the 1-position, unsubstituted or substituted benzyl or unsubstituted or substituted 2-phenylethyl; phenyl may be mono- or polysubstituted by halogen, especially chlorine or fluorine. If the phenyl is polysubstituted, the substituents may be different. The 2-phenylethyl radicals may also be substituted in the 2-position on the ethyl by alkylmercapto of 1 to 6 carbon atoms, especially n-butylmercapto and isobutylmercapto, by alkenylmercapto of 2 to 6 carbon atoms, especially allylmercapto, by phenylmercapto which may bear halogen substituents, especially chlorine, on the phenyl ring, or by halogen, especially chlorine. If the 2-phenylethyl radical is substituted in the 2-position by halogen, the phenyl ring bears at least one halogen substituent.

Suitable salts of triazole derivatives of the formula I are those with inorganic or organic acids. Examples of such acids are hydrogen halides, especially hydrogen chloride and hydrogen bromide, nitric acid, sulfuric acid, oxalic acid, trichloroacetic acid, and aryl- or alkylsulfonic acids, especially p-toluenesulfonic acid and dodecylbenzenesulfonic acid.

Examples of triazole derivatives suitable as synergists are 1-[2-chloro-2-(4-fluorophenyl)-ethyl]-1,2,4-triazole, 1-[2-chloro-2-(4-chlorophenyl)-ethyl]-1,2,4-triazole, 1-[2-chloro-2-(2,4-dichlorophenyl)-ethyl]-1,2,4-triazole, 1-[2-n-butylmercapto-2-(2,4-dichlorophenyl)-ethyl]-1,2,4-triazole, 1-[2-isobutylmercapto-2-(2,4-dichlorophenyl)-ethyl]-1,2,4-triazole, 1-[2-allylmercapto-2-(2,4-dichlorophenyl)-ethyl]-1,2,4-triazole, 1-[2-bromo-2-(2,4-dichlorophenyl)-ethyl]-1,2,4-triazole, 1-benzyl-1,2,4-triazole, 1-(4-chlorobenzyl)-1,2,4-triazole, 1-(2-chlorobenzyl)-1,2,4-triazole, 1-(2-phenylethyl)-1,2,4-triazole, and 1-[2-(4-chlorobenzyl)-mercapto-2-(2,4-dichlorophenyl)-ethyl]-1,2,4-triazole, and salts, especially the hydrochlorides, of these triazole derivatives.

Triazole derivatives of the formula I in which R denotes

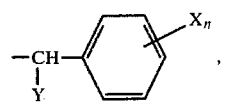

Y and X denoting halogen and n denoting one of the integers 1 and 2, their manufacture, and the use thereof as fungicides are disclosed in German Laid-Open Application DE-OS No. 2,547,954.

Triazole derivatives of the formula I in which R denotes unsubstituted or halogen-substituted phenyl may be obtained in conventional manner by reaction of 1,2,4-triazole with a benzyl halide which is optionally substituted by halogen on the phenyl ring.

Triazole derivatives of the formula I in which R denotes

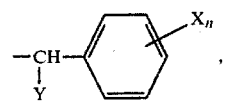

Y denoting halogen, are obtained in conventional manner by reaction of a 1-(2-hydroxy-2-phenylethyl)-1,2,4-triazole of the formula

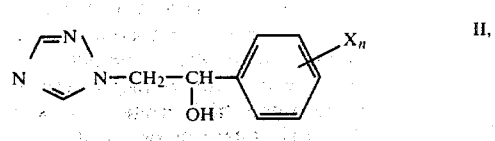

where X and n have the above meanings, with a halogenating agent, such as thionyl chloride, phosphorus trichloride, phosphorus tribromide, phosphorus pentachloride, and anhydrous hydrofluoric acid. The triazole salts obtained for instance in the form of their hydrochlorides may be converted into base form in conventional manner by reaction with a base, e.g., alkali metal hydroxide, alkali metal carbonate or ammonia.

Compounds of the formula II may be prepared by a reduction method, usually used for ketones, from the corresponding triazolyl alkanones of the formula

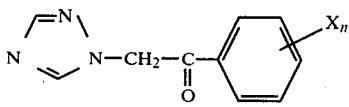

where X and n have the above meanings. The compounds of the formula III are known and may be obtained by reaction of 1,2,4-triazole with compounds of the formula

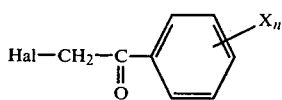

where X and n have the above meanings and Hal denotes chlorine or bromine (German Laid-Open Application De-OS No. 2,431,407).

Triazole derivatives of the formula I in which R is

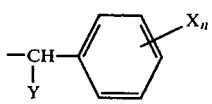

Y denoting alkylmercapto or alkenylmercapto, may be prepared by reaction of a 1-[2-halo-2-phenylethyl]-1,2,4-triazole of the formula

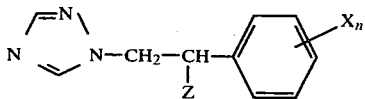

where Z and X denote halogen and n denotes one of the integers 1 and 2, with an alkyl or alkenyl mercaptide in a diluent. The mercaptide is obtained either before or during the reaction from the added mercaptan by reaction with a base. The sulfur compounds which are formed may be converted into the corresponding salts with strong acids.

The following examples illustrate the preparation of the triazole derivatives of the formula I.

EXAMPLE 1

12.55 parts by weight of butylmercaptan is dripped into a suspension of 3.33 parts by weight of sodium hydride in 180 parts by weight of tetrahydrofuran. A solution of 27.5 parts by weight of 1-[2-chloro-2-(2,4-dichlorophenyl)-ethyl]-1,2,4-triazole in 50 parts of tetrahydrofuran is then dripped in and the mixture is stirred for 3 days at room temperature. The mixture is concentrated, stirred with water, and extracted with dichloromethane. The resulting dichloromethane solution is dried and evaporated. There is obtained 29.5 parts of crude 1-[2-n-butylmercapto-2-(2,4-dichlorophenyl)-ethyl]-1,2,4-triazole, which is dissolved in ethyl acetate. When hydrogen chloride is passed into the ethyl acetate solution, 25.9 parts of 1-[2-n-butylmercapto-2-(2,4-dichlorophenyl)-ethyl]-1,2,4-triazole hydrochloride, m.p. 143° C., precipitates out.

EXAMPLE 2

A mixture of 34.2 parts by weight of benzyl bromide, 13.8 parts by weight of 1,2,4-triazole and 41.4 parts by weight of potassium carbonate in 150 parts by weight of acetonitrile is refluxed for 10 hours while stirring. The mixture is filtered and the filtrate is evaporated to dryness and recrystallized from a mixture of toluene and cyclohexane. There is obtained 21 parts by weight of 1-benzyl-1,2,4-triazole; m.p.: 58° C.

EXAMPLE 3

129 g of 1-(2-[2',4'-dichlorophenyl]-2-hydroxyethyl)-1,2,4-triazole is dissolved in 1 liter of chloroform and the solution is brought to the boil while stirring. 90 g of thionyl chloride is then slowly dripped in. After the mixture has been refluxed for several hours, it is allowed to cool; 1 liter of toluene is then added. The hydrochloride which precipitates out is filtered off and washed with petroleum ether. There is obtained 150 g of 1-(2-chloro-2-[2,4-dichlorophenyl]-ethyl)-1,2,4-triazole hydrochloride; m.p.: 100° C.

The following compounds may be prepared in the same way:

1-[2-chloro-2-(4-fluorophenyl)-ethyl]-1,2,4-triazole; viscous oil;

1-[2-isobutylmercapto-2-(2,4-dichlorophenyl)-ethyl]-1,2,4-triazole; viscous oil;

1-[2-isobutylmercapto-2-(2,4-dichlorophenyl)-ethyl]-1,2,4-triazole hydrochloride; m.p. 114° C.;

1-[2-allylmercapto-2-(2,4-dichlorophenyl)-ethyl]-1,2,4-triazole; viscous oil;

1-[2-allylmercapto-2-(2,4-dichlorophenyl)-ethyl]-1,2,4-triazole hydrochloride; m.p. 103° C.;

1-(4-chlorobenzyl)-1,2,4-triazole hydrochloride; m.p. 186° to 187° C.;

1-(2-chlorobenzyl)-1,2,4-triazole hydrochloride; m.p. 194° to 195° C.;

1-(2-phenylethyl)-1,2,4-triazole; b.p. 101° to 102° C./0.13 mbar;

1-(3-chlorobenzyl)-1,2,4-triazole hydrochloride; m.p. 161° to 162° C.;

1-[2-(4-chlorophenyl)-mercapto-2-(2,4-dichlorophenyl)-ethyl]-1,2,4-triazole; m.p. 72° C.;

1-[2-(4-chlorophenyl)-mercapto-2-(2,4-dichlorophenyl)-ethyl]-1,2,4-triazole hydrochloride; m.p. 176° to 178° C.;

1-[2-(3-bromophenyl)-2-(4-chlorophenylmercapto)-ethyl]-1,2,4-triazole hydrochloride; m.p. 172° to 173° C.;

1-[2-(4-chlorophenylmercapto-2-(2,4-dichlorophenyl)-ethyl]-1,2,4-triazole oxalate; m.p. 155° C.;

1-[2-bromo-2-(2,4-dichlorophenyl)-ethyl]-1,2,4-triazole; m.p. 97° C.

Examples of insecticidal active ingredients the effectiveness of which can be increased by the triazole derivatives of the formula I are carbamates, such as aryl-N-methylcarbamates, N,N-dimethylcarbamates or hydroxyheterocycles or of enols, oxime carbamates, e.g., 1-naphthyl-N-methylcarbamate, m-tolyl-N-methylcarbamate, 2-isopropylphenyl-N-methylcarbamate, 2-sec.- butylphenyl-N-methylcarbamate, 3-(1-methylbutyl)-phenyl-N-methylcarbamate, o-chlorophenyl-N-methylcarbamate, 3,4-dimethylphenyl-N-methylcarbamate, 3,5-diethylphenyl-N-methylcarbamate, 3-isopropyl-5-methylphenyl-N-methylcarbamate, 6-chloro-3,4-xylyl-N-methylcarbamate, 3,5-di-tert.-butylphenyl-N-methylcarbamate, 3,4,5-trimethylphenyl-N-methylcarbamate, 2-isopropylphenyl-N-methylcarbamate, 3,5-dimethyl-4-methylmercaptophenyl-N-methylcarbamate, 4-dimethylamino-m-tolyl-N-methylcarbamate, 4-dimethylamino-3,5-xylyl-N-methylcarbamate, 4-diallylamino-3,5-dimethylphenyl-N-methylcarbamate, 2-(1,3-dioxolan-2-yl)-phenyl-N-methylcarbamate, 4-benzothienyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 1-isopropyl-3-methyl-5-pyrazolyl-N,N-dimethylcarbamate, 2-dimethylcarbamoyl-3-methylpyrazolyl-(5)-N,N-dimethylcarbamate, 2-dimethylamino-5,6-dimethyl-4-pyrimidinyl-N,N-dimethylcarbamate, 2-(1-methoxy-2-chloro)-ethoxyphenyl-N-methylcarbamate, 3-[[(dimethylamino)-carbonyl]-oxy]-1,4-dimethyl-4-propyl-2-pyrazin-5-one, 2-methyl-2-(methylthio)-propionaldehyde-O-(methylcarbamoyl)-oxime, S-methyl-N-[(methylcarbamoyl)]-oxy-thioacetimidate, S-2-cyanoethyl-N-[(methylcarbamoyl)-oxy]-thioacetimidate, methyl-N',N'-dimethyl-M-[(methylcarbamoyl)-oxy]-1-thiooxamimidate, 2,4-dimethyl-1,3-dithiolane-2-carboxaldehyde-O-(methylcarbamoyl)-oxime, 3-(dimethylaminomethyleneimino)-phenyl-N-methylcarbamate, 4-(dimethylaminomethyleneimino)-m-tolyl-N-methylcarbamate, and 2-ethylthiomethylphenyl-N-methylcarbamate;

phosphoric or phosphonic acid esters and the corresponding thio or dithio esters, e.g., O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethylphosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-dimethyl-S-(ethylthio)-methylphosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfinylethyl)-phosphorothioate, O,O-diethyl-S-(2-ethylthioethyl)-phorphorodithioate, O,O-diethylthiophosphoryliminophenyl acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiodiazol-5-[4H]-onyl-(4)-methyl]-phosphorodithioate, O,O-diethyl-O-[3,5,6-trichloropyridyl-(2)]-phosphorothioate, O,O-dimethyl-O-(2-pyrazinyl)-phosphorothioate, O,O-diethyl-O-[2-isopropyl-4-methylpyridinyl-(6)]-phosphorothioate, O,O-dimethyl-O-[(2-diethylamino)-6-methyl-4-pyrimidinyl]-thionophosphate, O,O-dimethyl-S-(4-oxo-1,2,3-benzotriazin-3-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoramidothioate, O,S-dimethyl-N-acetylphosphoramidothioate, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethylphosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methylthiophenyl)-phosphorothioate, O-ethyl-O-(3-methyl-4-methylthiophenyl)-isopropylphosphoramidate, O,O-diethyl-O-[p-(methylsulfinyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethyl acetate phosphorodithioate, bis-(dimethylamino)-fluorophosphine oxide, octamethylpyrophosphoramide, O,O,O,O-tetraethyl dithiopyrophosphate, S-chloromethyl-O,O-diethylphosphorodithioate, O,O-ethyl- S,S-dipropyl-phosphorodithioate, O,O-dimethyl-O-2,2-dichlorovinyl phosphate, O,O-dimethyl-1,2-dibromo-2,2-dichloroethyl phosphate, O,O-dimethyl-2,2,2-trichloro-1-hydroxyethyl phosphonate, and O,O-dimethyl-S-[1,2-biscarbethoxyethyl-(1)]-phosphorodithioate;

pyrethrins, e.g., an active ingredient mixture consisting of pyrethrin I, pyrethrin II, cinerin I and cinerin II from *Chrysanthemum cinerae* folium flowers;

synthetic pyrethroids, such as esters of 2,2-dimethyl-3-(2,2-dimethylvinyl)-cyclopropanecarboxylic acid, e.g., 2-allyl-3-methylcyclopenten-(2-on-1-yl-(4-chrysanthemate, 3,4,5,6-tetrahydrophthalimidomethyl-DL-cis,-trans-chrysanthemate, 5-benzylfuryl-(3)-methyl-DL-cis, trans-chrysanthemate, and 2-methyl-5-(2-propynyl)-3-furylmethyl-chrysanthemate, or esters of 2,2-dimethyl-3-(2,2-dihalovinyl)-cyclopropanecarboxylic acid, e.g., 3-phenoxybenzyl (+)-cis,trans-2,2-dimethyl-3-(2,2-dichlorovinyl)-cyclopropane-1-carboxylate, α-cyano-3-phenoxybenzyl (+)-cis,trans-2,2-dimethyl-3-(2,2-dichlorovinyl)-cyclopropanecarboxylate, and (s)-α-cyano-3-phenoxybenzyl-cis(1R,3R)-2,2-dimethyl-3-(2,2-dibromovinyl)-cyclopropanecarboxylate;

α-alkylphenyl acetates, e.g., α-isopropylphenyl acetates, especially α-cyano-3-phenoxybenzyl-α-isopropyl-4-chlorophenyl acetate, 3-phenoxybenzyl-α-isopropyl-4-chlorophenyl acetate, 5-benzyl-3-furylmethyl-α-isopropyl-4-chlorophenyl acetate, 5-benzyl-3-furylmethyl-α-isopropyl-4-methylphenyl acetate, 3-phenoxybenzyl-α-isopropyl-4-methylphenyl acetate, 3-phenoxybenzyl-α-isopropyl-4-methoxyphenyl acetate, and 5-benzyl-3-methylfuryl-α-isopropyl-4-methoxyphenyl acetate;

α-cyclopropylphenyl acetates, e.g., α-cyano-3-phenoxybenzyl-α-cyclopropyl-4-chlorophenyl acetate, 5-benzyl-3-furylmethyl-α-cyclopropyl-4-chlorophenyl acetate, and α-cyano-3-phenoxybenzyl-α-cyclopropyl-4-bromophenyl acetate;

and chlorinated hydrocarbons, e.g., γ-hexachlorocyclohexane, 1,1-di-(p-methoxyphenyl)-2,2,2-trichloroethane, and 6,7,8,9,10,10-hexachloro-1,5,5a,6,9,9a-hexahydro-6,9-methano-2,4,3-benzodioxathiepin-3-oxide.

Triazole derivatives, or salts thereof, and insecticidal active ingredients may be employed in the agents according to the invention in relatively wide ratios. However, a ratio outside the range of from 1:10 to 10:1 parts by weight will probably seldom be of use. The preferred ratio range is from 1:5 to 5:1 parts by weight.

The insecticidal agents according to the invention may be used on a variety of plant and household pests. They may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used. Triazole derivatives and insecticidal active ingredient, or formulations thereof, may be applied separately or together.

The formulations generally contain from 0.1 to 95, preferably 0.5 to 90, % by weight of active ingredient and synergist.

The amount of synergist and active ingredient in the ready-to-use formulations may vary within a wide range; it is generally from 0.0001 to 10%, preferably from 0.01 to 1%.

The agents according to the invention may also be successfully used in the ultra-low volume method, where it is possible to apply formulations containing more than 95% by synergist and active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the agents according to the invention (if desired, immediately before use (tankmix)) oils of various types, herbicides, fungicides, other insecticides, and bactericides. These agents may be added to the agents according to the invention in a ratio by weight of from 1:10 to 10:1.

The use of the insecticidal agents according to the invention facilitates the control of plant and household pests. Examples of these are injurious insects from the Lepidoptera order, e.g., *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleopteria order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappahis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae,* and *Megoura viciae;* and mites and ticks (Acarina) belonging to the Arachnida class, e.g., *Tetranychus urticae, Tetranychus atlanticus, Tetranychus pacificus, Paratetranychus pilosus, Bryobia praetiosa, Ixodes ricinus; Ornithodorus moubata, Ablyomma americanum, Dermacentor silvarum,* and *Boophilus microplus.*

The following biological experiments demonstrate the synergistic action. However, they should only be considered as examples, and in no way cover the whole range claimed.

The synergists employed are as follows:

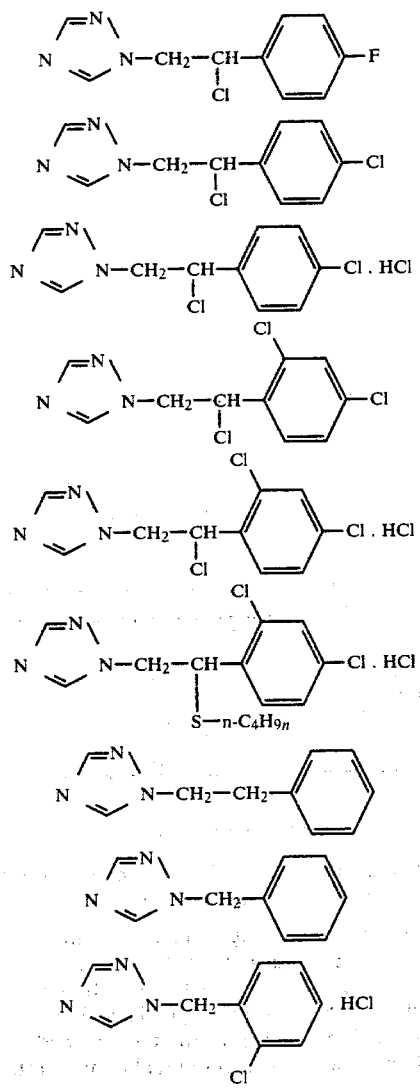

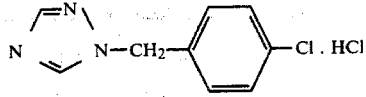

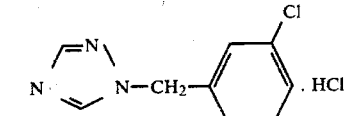

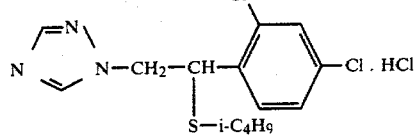

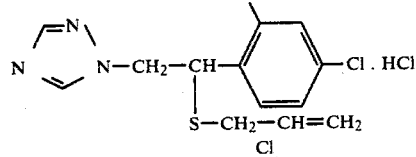

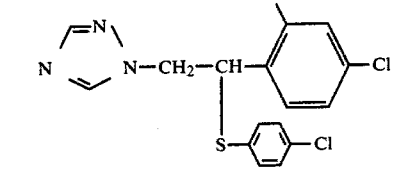

The insecticidal active ingredients employed were 1-naphthyl-N-methylcarbamate (carbaryl), 2,5-diethylphenyl-N-methylcarbamate (fenethcarb), 2-dimethylamino-5,6-dimethyl-4-pyrimidinyl-N,N-dimethylcarbamate (pirimicarb), 2-isopropoxyphenyl-N-methylcarbamate (propoxur), O,O-dimethyl-S-[1,2-bis-carbethoxyethyl-(1)]-phosphorodithioate (malathion), 3-phenoxybenzyl (±)-cis,trans-2,2-dimethyl-3-(2,2-dichlorovinyl)-cyclopropane-1-carboxylate (permethrin), and an active ingredient mixture consisting of pyrethrin I, pyrethrin II, cinerin I and cinerin II from Chrysanthemum cinerae folium flowers (hereinafter designated "pyrethrins").

EXAMPLE A

Synergistic action on oriental cockroaches (*Blatta orientalis*)

The bottom of 1-liter jars is treated with acetonic solutions of the insecticidal active ingredients and the synergists in the ratios given in the table below. After the solvent has evaporated, 5 adult cockroaches (*Blatta orientalis*) are placed in each jar, and the kill rate is determined after 48 hours.

The application rates are in logarithmic progression and permit a dose-effect curve to be drawn; the $LD_{50}$ is determined graphically and serves as a basis for assessment. I. The insecticide employed is carbaryl; the ratio of carbaryl to synergist is 1:5 parts by weight.

| Active ingredient | | LD 50 | | | |
|---|---|---|---|---|---|
| Carbaryl | | 0.25 | mg | | |
| No. 1 | | >10.0 | mg | | |
| Carbaryl | + No. 1 | 0.02 | mg | + 0.1 | mg |
| No. 2 | | 3.0 | mg | | |
| Carbaryl | + No. 2 | 0.025 | mg | + 0.13 | mg |
| No. 3 | | 3.0 | mg | | |
| Carbaryl | + No. 3 | 0.021 | mg | + 0.105 | mg |

-continued

| Active ingredient | | LD 50 | |
|---|---|---|---|
| No. 4 | | >5.0 | mg |
| Carbaryl + No. 4 | | 0.03 | mg + 0.15 mg |
| No. 5 | | >5.0 | mg |
| Carbaryl + No. 5 | | 0.034 | mg + 0.17 mg |
| No. 6 | | >5.0 | mg |
| Carbaryl + No. 6 | | 0.1 | mg + 0.5 mg |
| No. 7 | | >2.0 | mg |
| Carbaryl + No. 7 | | 0.013 | mg + 0.065 mg |
| No. 8 | | >2.0 | mg |
| Carbaryl + No. 8 | | 0.027 | mg + 0.135 mg |
| No. 9 | | >2.0 | mg |
| Carbaryl + No. 9 | | 0.022 | mg + 0.11 mg |
| No. 10 | | >2.0 | mg |
| Carbaryl + No. 10 | | 0.015 | mg + 0.075 mg |
| No. 11 | | >2.0 | mg |
| Carbaryl + No. 11 | | 0.014 | mg + 0.07 mg |
| No. 12 | | >2.0 | mg |
| Carbaryl + No. 12 | | 0.035 | mg + 0.175 mg |
| No. 13 | | >2.0 | mg |
| Carbaryl + No. 13 | | 0.03 | mg + 0.15 mg |
| Fenvalerate | | 0.0033 | mg |
| No. 14 | | 2.0 | mg |
| Fenvalerate + No. 14 | | 0.001 | mg + 0.005 mg |

II. Use of various insecticides and different active ingredient:synergist ratios

| Active ingredient | | weight ratio active ingredient:synergist | LD 50 | |
|---|---|---|---|---|
| Carbaryl | | | 0.25 | mg |
| No. 1 | | | approx. 10 | mg |
| Carbaryl + No. 1 | | 5:1 | 0.009 | mg + 0.018 mg |
| Carbaryl + No. 1 | | 1:1 | 0.07 | mg + 0.07 mg |
| Carbaryl + No. 1 | | 1:1 | 0.07 | mg + 0.018 mg |
| Pirimicarb | | | approx. 25 | mg |
| Pirimicarb + No. 1 | | 5:1 | 7.0 | mg + 1.5 mg |
| Pirimicarb + No 1 | | 1:1 | 0.9 | mg + 0.9 mg |
| Pirimicarb + No. 1 | | 1:5 | 0.52 | mg + 2.6 mg |
| Fenethcarb | | | 0.66 | mg |
| Fenethcarb + No.1 | | 5:1 | 0.13 | mg + 0.026 mg |
| Fenethcarb + No. 1 | | 1:1 | 0.086 | mg + 0.086 mg |
| Fenethcarb + No. 1 | | 1:5 | 0.038 | mg + 0.19 mg |
| Pyrethrine | | | 0.088 | mg |
| Pyrethrins + No. 1 | | 1:1 | 0.055 | mg + 0.055 mg |
| Pyrethrins + No. 1 | | 1:5 | 0.036 | mg + 0.18 mg |
| Permethrin | | | 0.045 | mg |
| Permethrin + No. 1 | | 1:1 | 0.028 | mg + 0.028 mg |

EXAMPLE B

Synergistic action on houseflies (*Musca domestica*)

Both covers and bottoms of Petri dishes 10 cm in diameter are lined with a total per dish of 2 ml of acetonic solutions of the active ingredients. After the solvent has evaporated (about 30 mins.), 10 flies are introduced into each dish.

The kill rate is determined after 4 hours and the $LD_{50}$ is determined graphically.

| Active ingredient | Weight ratio active ingredient: asynergist | $LD_{50}$ | |
|---|---|---|---|
| Carbaryl | | 7.0 | mg |
| No. 1 | | 5.0 | mg |
| Carbaryl + No. 1 | 5:1 | 0.8 | mg + 0.16 mg |
| Carbaryl + No. 1 | 1:5 | 0.2 | mg + 1.0 mg |
| Pyrethrins | | 0.015 | mg |
| No. 2 | | 0.3 | mg |
| Pyrethrins + No. 2 | 1:5 | 0.0055 | mg + 0.0275 mg |
| No. 4 | | >2.0 | mg |

-continued

| Active ingredient | Weight ratio active ingredient: asynergist | $LD_{50}$ | |
|---|---|---|---|
| Pyrethrins + No. 4 | 1:5 | 0.009 | mg + 0.045 mg |
| No. 5 | | >2.0 | mg |
| Pyrethrins + No. 5 | 1:5 | 0.0095 | mg + 0.0475 mg |
| No. 6 | | >2.0 | mg |
| Pyrethrins + No. 6 | 1:5 | 0.006 | mg + 0.3 mg |
| No. 8 | | >2.0 | mg |
| Carbaryl + No. 8 | 0.1 | mg + 0.1 | mg |

EXAMPLE C

Contact action on houseflies (*Musca domestica*)

1 μl of the active ingredient dissolved in acetone is administered to the ventral abdomen of 4-day old imagoes under slight $CO_2$ narcosis. 20 animals treated in the same way are then placed in a cellophane bag having a volume of approximately 500 ml.

After 4 hours the kill rate is determined, a dose-mortality curve is drawn from the different concentrations, and the $LD_{50}$ is worked out.

| Active ingredient | LD 50 | |
|---|---|---|
| No. 1 | 10.0 | μg /fly ineffective |
| Fenethcarb | 0.16 | μg/fly |
| Fenethcarb + No. 1 | 0.09 | μg + 0.45 μg/fly |
| Malathion | 0.53 | μg/fly |
| Malathion + No. 1 | 0.38 | μg + 1.9 μg/fly |
| Permethrin | 0.006 | μg/fly |
| Permethrin + No. 1 | 0.0046 | μg +0.0046 μg/fly |

EXAMPLE D

Synergistic action on caterpillars of the diamondback moth (*Plutella maculipennis*)

Leaves of young cabbage plants are dipped for 3 seconds in aqueous emulsions of the active ingredients, and, after excess liquid has briefly been allowed to drip off, placed on a moist filter paper in a Petri dish. 10 caterpillars in the 4th stage are then placed on the leaves. The kill rate at the individual concentrations is ascertained after 48 hours, and the $LC_{50}$ is calculated therefrom.

| Active ingredient | | LC 50 | |
|---|---|---|---|
| No. 1 | | 0.25 % | |
| Carbaryl | | 0.16 % | |
| Carbaryl | + No. 1 | 0.03 % | + 0.03 % |
| Pirimicarb | | 0.25 % | |
| Pirimicarb | + NO. 1 | 0.11 % | + 0.11 % |
| Propoxur | | 0.025 % | |
| Propoxur | + No. 1 | 0.006 % | + 0.006 % |
| Malathion | | 0.0035 % | |
| Malathion | + No. 1 | 0.002 % | + 0.001 % |

EXAMPLE E

Synergistic action on granary weevils (*Sitophilus granarius*)

Petri dishes 10 cm in diameter are lined with acetonic solutions of the active ingredients. After the solvent has evaporated, 50 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

| Active ingredient | | LD 50 | | |
|---|---|---|---|---|
| Carbaryl | | 2.5 | mg | |
| No. 1 | | 2.0 | mg ineffective | |
| Carbaryl | + No. 1 | 0.1 | mg + 0.1 | mg |
| | | 0.055 | mg + 0.275 | mg |
| NO. 8 | | 2 | mg ineffective | |
| Carbaryl | + No. 8 | 0.4 | mg + 2 | mg |
| No. 10 | | 5 | mg ineffective | |
| Carbaryl | + No. 10. | 1.3 | mg + 6.5 | mg |
| Propoxur | | 7 | mg | |
| Propoxur | + No. 1 | 1.25 | mg + 1.25 | mg |
| Fenvalerate | | 0.16 | mg | |
| Fenvalerate | + No. 1 | 0.054 | mg + 027 | mg |
| Pyrethrins | | 1.2 | mg | |
| Pyrethrins | + No. 1 | 0.8 | mg + 0.8 | mg |
| No. 12 | | 5 | mg ineffective | |
| Carbaryl | + No. 12 | 0.2 | mg + 1.1 | mg |
| No. 13 | | 5 | mg ineffective | |
| Carbaryl | + No. 13 | 0.11 | mg + 0.55 | mg |

We claim:

1. An insecticidal agent containing an insecticidally effective amount of a mixture of a triazole derivative of the formula

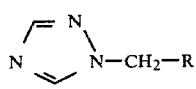

wherein R denotes unsubstituted or halogen-substituted phenyl, or

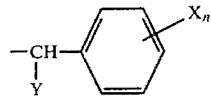

Y denoting hydrogen, halogen, alkylmercapto of 1 to 6 carbon atoms, alkenylmercapto of 2 to 6 carbon atoms, or unsubstituted or halogen-substituted phenylmercapto, X denoting halogen, and n denoting one of the integers zero, 1 and 2, with the proviso that n does not denote zero when Y is halogen, or a salt of a triazole derivative of formula I, and an insecticidal active ingredient selected from the group consisting of one or more carbamates, the ratio of the triazole derivative of formula I, or a salt of said triazole, to the insecticidally active ingredient is from 1:10 to 10:1 parts by weight.

2. An insecticidal agent as set forth in claim 1, containing a triazole derivative of the formula I in which Y denotes chlorine.

3. An insecticidal agent as set forth in claim 1, containing a triazole derivative of the formula I in which Y denotes alkylmercapto of 1 to 6 carbon atoms.

4. An insecticidal agent as set forth in claim 1, wherein the triazole derivative of the formula I is 1-[2-chloro-2-(4-fluorophenyl)-ethyl]-1,2,4-triazole.

5. A process for combating insects, wherein the insects or their biotope are treated with an insecticidal agent containing an insecticidally effective amount of a mixture of a triazole derivative of the formula

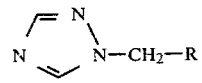

where R denotes unsubstituted or halogen-substituted phenyl, or

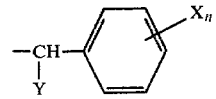

Y denoting hydrogen, halogen, alkylmercapto of 1 to 6 carbon atoms, alkenylmercapto of 2 to 6 carbon atoms, or unsubstituted or halogen-substituted phenylmercapto, X denoting halogen, and n denoting one of the integers zero, 1 and 2, with the proviso that n does not denote zero when Y is halogen, or a salt of a triazole derivative of the formula I, and an insecticidal active ingredient selected from the group consisting of one or more carbamates, the ratio of the triazole derivative of formula I, or a salt of said triazole, to the insecticidally active ingredient is from 1:10 to 10:1 parts by weight.

6. A process for combating insects as set forth in claim 5, in which Y denotes chlorine in the triazole derivative formula I.

7. A process for combating insects as set forth in claim 5, in which Y denotes alkylmercapto of 1 to 6 carbon atoms in the triazole derivative of formula I.

8. A process for combating insects as set forth in claim 5, in which the triazole derivative of formula I is 1-[2-chloro-2-(4-fluorophenyl)-ethyl]-1,2,4-triazole.

* * * * *